US008002759B2

(12) United States Patent
Andersen et al.

(10) Patent No.: US 8,002,759 B2
(45) Date of Patent: Aug. 23, 2011

(54) OSTOMY APPLIANCE

(75) Inventors: Birthe Vestbo Andersen, Espergaerde (DK); Soeren Hansen, Helsingoer (DK); Eskil Holland Olsen, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/480,471

(22) PCT Filed: Jun. 13, 2002

(86) PCT No.: PCT/DK02/00400
§ 371 (c)(1),
(2), (4) Date: Dec. 12, 2003

(87) PCT Pub. No.: WO02/102289
PCT Pub. Date: Dec. 27, 2002

(65) Prior Publication Data
US 2004/0171999 A1    Sep. 2, 2004

(30) Foreign Application Priority Data
Jun. 15, 2001 (DK) .................................. 2001 00935

(51) Int. Cl.
*A61F 5/44* (2006.01)
(52) U.S. Cl. ........................................ 604/343; 604/332
(58) Field of Classification Search ........... 604/332–345
See application file for complete search history.

(56) References Cited

U.S. PATENT DOCUMENTS

| | | | |
|---|---|---|---|
| 2,520,831 A * | 8/1950 | Chincholl ....................... 604/335 |
| 3,618,606 A | 11/1971 | Brown et al. |
| 3,837,342 A | 9/1974 | Mitsuo ........................... 128/283 |
| 4,233,977 A * | 11/1980 | Mattson ........................ 604/335 |
| 4,330,060 A * | 5/1982 | Thornton .................... 206/459.5 |
| 4,331,148 A * | 5/1982 | Steer et al. ..................... 604/333 |
| 4,367,732 A | 1/1983 | Poulsen et al. ................. 128/156 |
| 4,445,898 A | 5/1984 | Jensen |
| 4,543,097 A | 9/1985 | Van Polen ...................... 604/333 |
| 5,051,259 A | 9/1991 | Olsen et al. .................... 424/443 |
| 5,248,308 A * | 9/1993 | von Emster .................... 604/337 |
| 5,714,225 A | 2/1998 | Hansen et al. ................. 428/114 |
| 5,800,415 A | 9/1998 | Olsen ............................. 604/336 |
| 5,865,819 A | 2/1999 | Cisko et al. |
| 6,336,918 B1 * | 1/2002 | Olsen et al. .................... 604/332 |
| 6,419,664 B1 * | 7/2002 | von Bulow et al. ........... 604/337 |
| 6,516,469 B1 * | 2/2003 | Schaetzel ............................ 2/16 |
| 6,589,222 B1 | 7/2003 | Olsen |
| 6,858,023 B2 * | 2/2005 | Poulsen .......................... 604/335 |
| 6,902,551 B2 | 6/2005 | Hansen et al. |
| 2003/0073962 A1 * | 4/2003 | Olsen et al. .................... 604/327 |
| 2004/0030314 A1 * | 2/2004 | LaVon et al. ................... 604/380 |
| 2005/0159717 A1 * | 7/2005 | Holtermann .................... 604/332 |

FOREIGN PATENT DOCUMENTS

DK         158969         8/1990
(Continued)

*Primary Examiner* — Michele Kidwell
(74) *Attorney, Agent, or Firm* — Coloplast Corp., Coloplast A/S; Daniel G. Chapik; Nicholas R. Baumann

(57) ABSTRACT

A disposable ostomy receiving bag having front and rear walls sealed together along the rim thereof and having a top end and a bottom end, and a cover of a sheet material covering one or both surfaces of the bag and only secured to the wall along the part of the rim being superimposed on the sealed rim of the front and rear walls. The bottom end can be folded to reduce the size of the bag, with the folded end discreetly hidden under the cover sheet. Should a larger collecting volume be needed, unfolding of the bag allows for an easy enlargement of the active volume of the bag simply by withdrawing the end of the bag from under the cover sheet.

23 Claims, 4 Drawing Sheets

FOREIGN PATENT DOCUMENTS

| | | |
|---|---|---|
| GB | 2 094 153 | 9/1982 |
| GB | 2 247 172 | 2/1992 |
| GB | 2 268 065 | 1/1994 |
| GB | 2340398 | 2/2000 |
| HU | 0105101 | 4/2002 |
| HU | 0300624 | 7/2003 |
| WO | 93/18725 | 9/1993 |
| WO | 94/18919 | 9/1994 |
| WO | 97/39705 | 10/1997 |
| WO | WO 9966859 A2 * | 12/1999 |

* cited by examiner

OSTOMY APPLIANCE

This is a nationalization of PCT/DK02/00400 filed Jun. 13, 2002 and published in English.

BACKGROUND OF THE INVENTION

1. Field of the Invention

The present invention relates to a collecting bag to be secured to the abdomen of a patient or to a body side ostomy member for collecting fluids or excretions emerging from an abdominal stoma.

In connection with surgery for a number of diseases in the gastro-intestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

Ostomy receiving bags are available in various sizes for taking into account the different need for collecting capacity of the users, both the difference between different users and also for the individual user according to actual situation and diet. The different sizes may also allow the user to use a small bag or cap for discretion when e.g. when going out or attending public meetings.

However, as the secretion of exudates from the stoma cannot be regulated at will, situations often occur where the actual size of a more discreet collecting bag is not sufficient which may cause severe embarrassment for the user.

Thus, there is a need for a very discreet collecting bag which also offers a solution to an acute demand for a larger capacity of the collecting device.

2. Description of the Related Art

GB 2 247 172 discloses a disposable ostomy receiving bag comprising front and rear walls sealed together along the rim thereof and having a top end and a bottom end wherein the top end of the rear wall is provided with an inlet opening, wherein the rear wall of the receiving bag is provided with a further cover of a sheet material which cover layer terminates at a lower edge thereof.

GB 2 094 153 discloses a disposable ostomy receiving bag comprising front and rear walls sealed together along the rim thereof and having a top end and a bottom end wherein the top end of the rear wall is provided with an inlet opening, wherein the rear wall of the receiving bag is provided with a further cover of a sheet material, which cover layer is secured to the lower part of the wall.

None of the references disclose nor indicate a solution to the problem of having an ostomy receiving bag which may be small and discrete and which at the same time also offers the option of providing a larger capacity if needed.

SUMMARY OF THE INVENTION

The present invention relates to a disposable ostomy receiving bag comprising front and rear walls sealed together along the rim thereof and having a top end and a bottom end wherein the top end of the rear wall is provided with an inlet opening, wherein the receiving bag Is provided with a further cover of a sheet material covering one or both surfaces thereof.

BRIEF DESCRIPTION OF THE DRAWINGS

The invention is disclosed more in detail with reference to the drawings in which.

DETAILED DESCRIPTION OF THE PRESENT INVENTION

Figure 1:
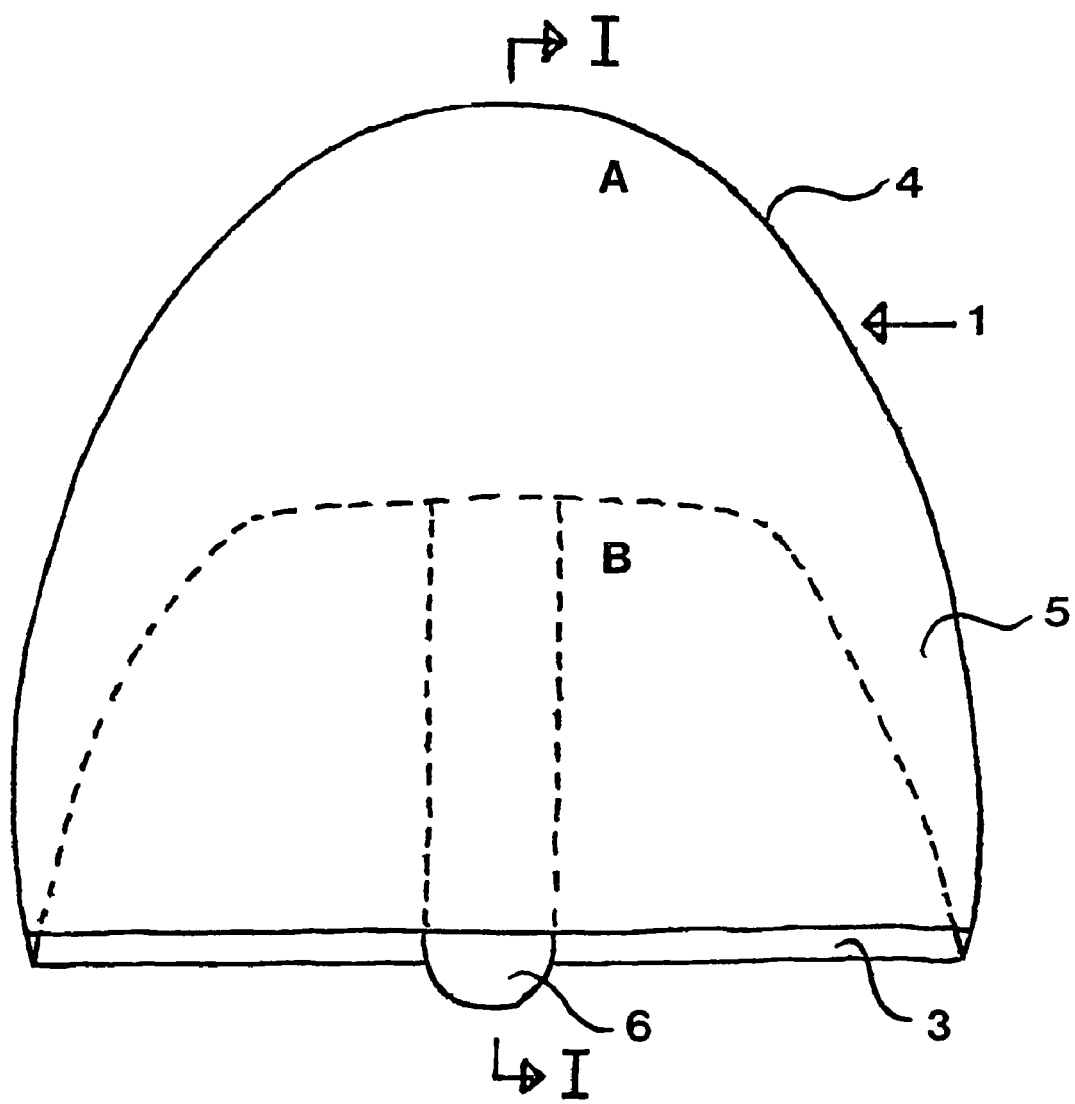
FIG. 1 shows an embodiment of an ostomy receiving bag according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a disposable ostomy receiving bag comprising front and rear walls sealed together along the rim thereof and having a top end and a bottom end, with the top end of the rear wall being provided with an inlet opening. The receiving bag is provided with a further cover of a sheet material covering at least one of the surfaces thereof, wherein the cover sheet is provided with an unattached or cut edge defining a part of the cover which only covers a part of the corresponding wall and is only secured to the wall along the part of the rim being superimposed on the sealed rim of the front and rear walls. The receiving bag is characterised in that the bottom end of the bag is folded back and stretches under the cover sheet.

Thus, the present invention relates to a collecting bag to be secured to the abdomen of a patient or to a body side ostomy member for collecting fluids or excretions.

One embodiment of the invention, in which the cut cover sheet only covers the corresponding surface partly, offers an option of folding the bag and putting the folded part under the cover sheet. This folding reduces the size of the bag and keeps the folded end discreetly hidden under the cover sheet and thus ensures discretion. Furthermore, it allows for an easy enlargement of the active volume of the bag simply by withdrawing the end of the bag from under the cover sheet, should a larger collecting volume suddenly be needed in situations where there is difficult or no access to a rest room.

When the cover sheet of the front wall is cut along a line perpendicular to the longest dimension of the front wall the end of the bag is easy to insert and withdraw from behind the cover sheet.

In a preferred embodiment the cover sheet covers the front wall.

It is preferred that the cover sheet of the front wall superimposing the top end of the front wall forms a pocket which will not give rise to folding of the top part of the cover sheet.

It has been found suitable when the length of the cover sheet of the front wall is from 25 to 100% of the longest dimension of the front wall which still allows for a considerable temporary reduction of the volume of the bag and reduces the use of raw materials. Thus, it is foreseen that the cover sheet may be in the form of a band covering a part of the front wall.

It is preferred that the unattached or cut edge of the cover sheet of the front wall is placed at a length of from 50% to 75% of the longest dimension of the front wall. With this placement range, the length of the longest dimension is reduced by 50% to 25%, respectively, when the bottom end of the bag is folded and placed under the unattached or cut edge of the cover sheet.

In an another embodiment of the invention, the cover sheet being cut covers all of the surface of the corresponding wall and is secured to the wall along the part of the rim being superimposed on the sealed rim of the front and rear walls leaving a slit defining two pockets each covering an end part of the bag.

In a further preferred embodiment of the invention the end of the bag opposite the top end is provided with a strip of material extending from the bottom end which will render it easier to grasp and withdraw the folded end of the bag from behind the cover sheet.

It is especially preferred that the length of the strip is longer than the distance from the bottom end of the bag in its folded state to the cut off line or unattached edge of the cover sheet as the end of the strip will then protrude from behind the cover sheet and thus be easier to grasp.

Furthermore, it is preferred to secure the strip in a manner that allows an easy removal, so that it e.g. can be torn off, naturally without risk of damaging the welding of the pouch which might lead to leaks, after the expansion or unfolding of the bag in order to reduce any discomfort by the strip stretching from below the pouch in the unfolded state. Thus, it is preferred that the ultimate strength of the strip in the area in which it is secured to the pouch is lower than the tearing strength of the welding of the rim of the pouch.

This may be achieved by securing the strip to the rim of the bag using a welding being weaker than the welding of the rim of the pouch and also weaker than the ultimate strength of the strip itself. Alternatively, the strip may be provided with one or more notches or perforations near the area in which it is secured to the pouch in order to ensure that the ultimate strength in this area is lower than the tearing strength of the welding of the rim of the pouch. The strip may be of any suitable material being compatible with the cover sheet and fulfilling the above requirements.

It is preferred that the cover sheet is of a porous material as such material may reduce noise from the bag and improve the "breathing" of the skin covered by the bag.

The ostomy receiving bag according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy receiving bag according to the invention may, as an alternative, be adapted for use directly (1-piece appliance) in which case the bag is provided with an adhesive wafer for securing the receiving bag to the user's skin, said bag and wafer having an inlet opening for receiving a stoma.

The receiving bag itself comprising front and rear walls sealed together along the rim and provided with an inlet opening may be made in analogy with and from materials conventionally used for the preparation of ostomy appliances. An ostomy body side member for use together with an ostomy receiving bag according to the invention may be produced from standard materials normally used for preparation of disposable ostomy and wound and incontinence devices.

Thus, the adhesive wafer for a body side member or of a 1-piece ostomy appliance bag according to the invention may be made from a medical grade barrier adhesives known in the such as the formulation being disclosed, for example in U.S. Pat. Nos. 4,367,732, 5,051,259 or 5,714,225. For a 2-piece ostomy appliance according to the invention the body side member and the receiving bag are provided with matching coupling means.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 93/18725 or WO 94/18919 or matching flanges for adhesive connection of the type disclosed in U.S. Pat. No. 5,800,415.

Suitable porous materials for use as cover for the purpose of the present invention are woven or non-woven sheet materials which are moisture resistant and may be united with materials conventionally used in the production of ostomy appliances such as non-woven materials of polyethylene, polypropylene or a polyester.

DESCRIPTION OF THE PREFERRED EMBODIMENTS

The invention is now explained more in detail with reference to the drawings showing preferred embodiments of the invention.

In FIG. 1 of the drawings is shown an embodiment of a disposable ostomy receiving bag (1) according to the invention comprising front and rear walls (3) sealed together along the rim (4) thereof and having a top end (A) and a bottom end wherein the top end of the rear wall is provided with an inlet opening (not shown), wherein the receiving bag is provided with a further cover of a sheet (5) material covering one or both surfaces thereof wherein the cover sheet at least one of the surfaces only covers a part of the corresponding wall and is only secured to the wall along the part of the rim (4) being superimposed on the sealed rim of the front and rear walls. The bottom end (B) is folded back and stretches under the cover sheet (5) of the front wall as indicated through a dotted line and is provided with a strip (6) of a sheet material extending from the bottom end. As can be seen in FIG. 1, when the bottom end of the bag is folded and placed under the cover sheet, the bag size and collecting capacity are at least 25% smaller than when the bag is unfolded.

Figure 2:
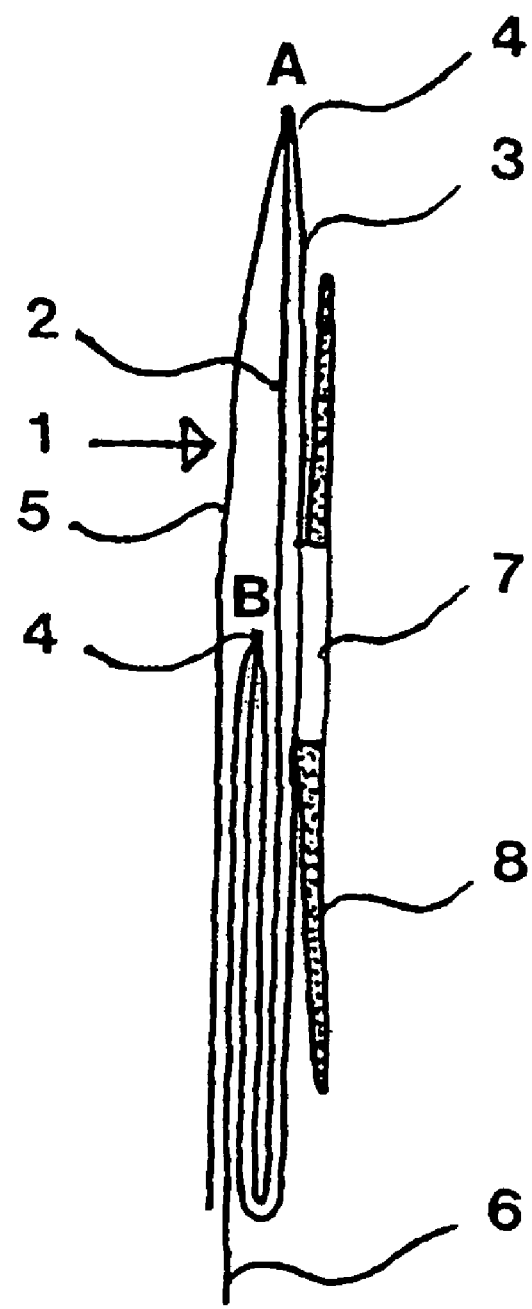
FIG. 2 shows a sectional view along the line I-I of the embodiment of FIG. 1.

FIG. 2 shows a sectional view along the line I-I of the embodiment of FIG. 1, showing the front (2) and rear (3) walls sealed together along the rim (4) thereof and having a top end (A) and a bottom (B) end wherein the top end of the rear wall is provided with an inlet opening (7), wherein the receiving bag is provided with a further cover (5) of a sheet material covering one or both surfaces thereof wherein the cover sheet at at least one of the surfaces only covers a part of the corresponding wall and is only secured to the wall along the part of the rim (4) being superimposed on the sealed rim of the front and rear walls. The bottom end (B) is folded back and stretches under the cover sheet (5) of the front wall and is provided with a strip (6) of a sheet material extending from the bottom end. Furthermore, the ostomy receiving bag (1) is provided with an adhesive wafer (8) for securing the same to the skin of an ostomate or to a body side member.

Figure 3:
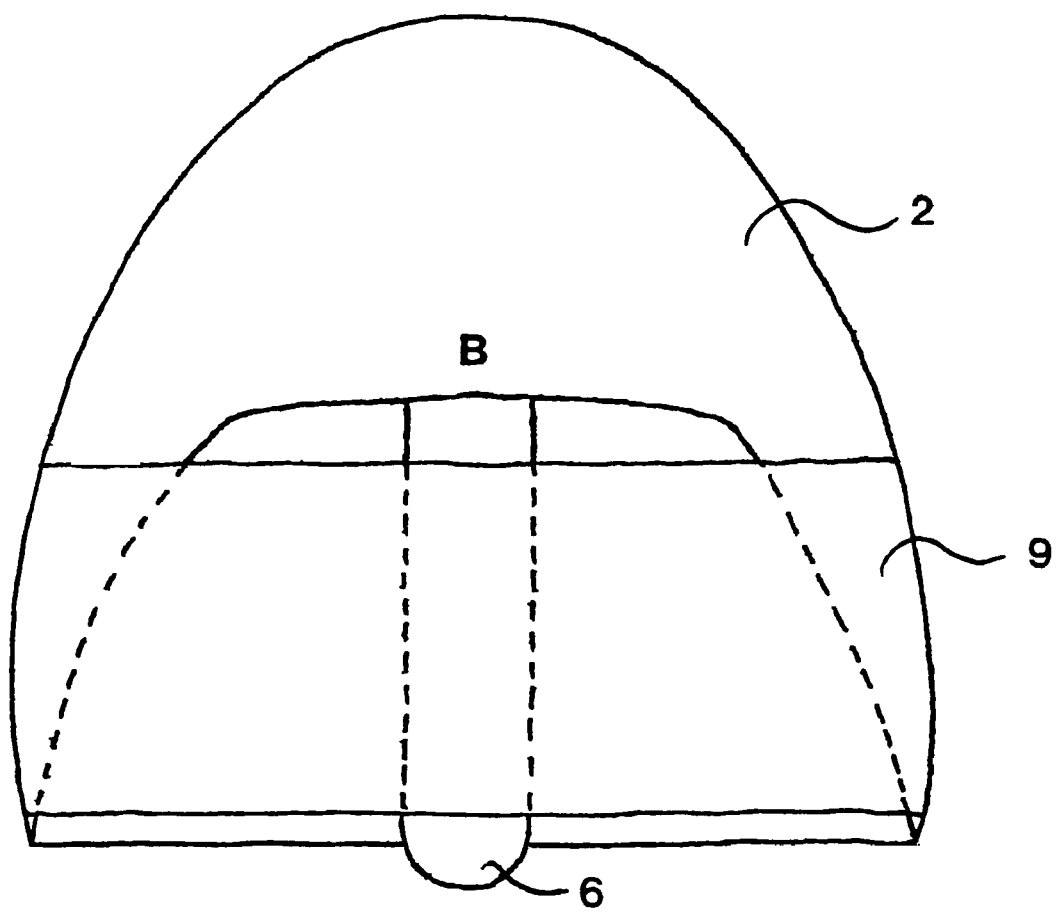
FIG. 3 shows a further embodiment of an ostomy receiving bag according to the invention.

FIG. 3 shows a further embodiment of an ostomy receiving bag according to the invention wherein the cover sheet of the front wall (2) is cut off, i.e., has an unattached edge, at a length of from 25% to 80% of the longest dimension of the front wall and is in the form of a band (9) covering a part of the front wall. The bottom end (B) being folded back and stretching under the cover sheet (9) of the front wall (2) and the end of the strip (6) of a sheet material are visible above and below the cover sheet.

Figure 4:
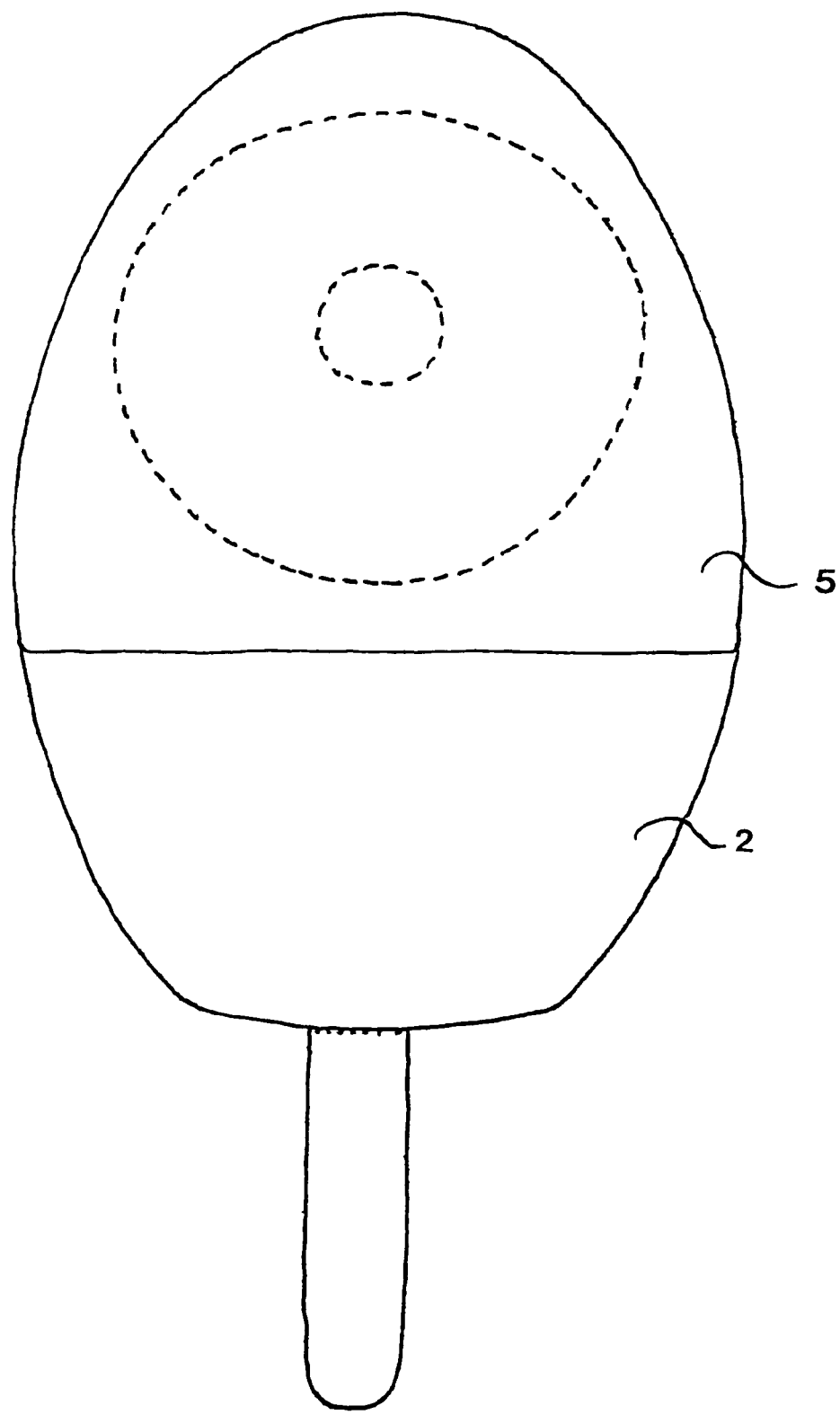
FIG. 4 shows the embodiment of FIG. 1 in an unfolded state, seen from the surface facing away from the user.

FIG. 4 shows the embodiment of FIG. 1 in an unfolded state, seen from the surface facing away from the user showing the front wall (2), the cover sheet (5) and the strip (6) extending from the bottom end and indicating an adhesive wafer situated on the back wall.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A disposable ostomy receiving bag comprising front and rear walls sealed permanently together continuously along an entirety of a rim thereof and having a top end bounded by an uppermost edge of the bag defined by a first portion of the sealed rim and a bottom end bounded by a lowermost edge of the bag defined by a second portion of the sealed rim, said top end of the rear wall being provided with an inlet opening, said receiving bag including a cover of a sheet material covering at least part of one of said walls, said cover sheet covering only a portion of a top end of the corresponding wall to form a pocket and being provided with an unattached or cut edge placed at a first distance from said uppermost edge, the first distance being from 50% to 75% of a longest dimension of said front wall extending from said uppermost edge to said lowermost edge, the bottom end of the bag being folded back and extending under the cover sheet to form a reduced collecting volume for said bag when folded.

2. The receiving bag as claimed in claim 1 wherein the cover sheet covers the front wall.

3. The receiving bag as claimed in claim 1 wherein said unattached or cut edge extends along a line generally perpendicular to said longest dimension of the corresponding wall.

4. The receiving bag as claimed in claim 1 wherein the longest dimension of the front wall is reduced by 50% to 25% when the bottom end of the bag is folded and extended under said unattached or cut edge.

5. The receiving bag as claimed in claim 1 further comprising a strip of material extending from the bottom end.

6. The receiving bag as claimed in claim 5, wherein the ultimate strength of the strip in the area in which it is secured to the bag is lower than the tearing strength of the rim of the bag.

7. The receiving bag as claimed in claim 5 wherein a length of the strip is longer than the distance from the bottom end of the bag in its folded state to the unattached or cut edge of the cover sheet.

8. The receiving bag as claimed in claim 1 wherein the cover sheet is of a porous material.

9. A disposable ostomy receiving bag comprising front and rear walls sealed permanently and continuously together along an entirety of a rim thereof and having a top end bounded by an uppermost edge of said bag and a bottom end bounded by a lowermost edge of said bag, said bag defining a first length as measured from the uppermost edge to the lowermost edge and having a first collecting volume, said top end of the rear wall having an inlet opening, a cover sheet overlying at least a part of the front wall or the rear wall and being secured to the respective wall only along a part of said rim and positioned relative to the uppermost edge of said bag so as to retain said bag is in a folded state being folded back upon itself and placed under the cover sheet to reduce said first length and said first collecting volume of the bag by at least 25%.

10. The receiving bag as claimed in claim 9 wherein the cover sheet covers at least part of the front wall.

11. The receiving bag as claimed in claim 9 wherein said first length represents a longest longitudinal dimension of said bag, said cover sheet being cut along a line generally perpendicular to said longest dimension of the corresponding wall to define a cut edge.

12. The receiving bag as claimed in claim 10 wherein the cover sheet of the front wall superimposes the top end of the front wall and forms a pocket.

13. The receiving bag as claimed in claim 10 wherein a length of the cover sheet is from 25 to 100% of the first length of the front wall.

14. The receiving bag as claimed in claim 11 wherein said cut edge is placed at a length of from 50% to 75% of said longest longitudinal dimension.

15. The receiving bag as claimed in claim 9, wherein a strip of material extends from the bottom end.

16. The receiving bag as claimed in claim 15, wherein the rim of the bag is welded and a strength of the strip where it is secured to the bag is less than a tearing strength of the welding of the bag rim.

17. The receiving bag as claimed in claim 15 wherein a length of the strip is longer than the distance from the bottom end of the bag in its folded state to a lower edge of the cover sheet.

18. A disposable ostomy receiving bag comprising:
a front and a rear wall sealed together permanently and continuously along an entirety of a rim thereof and having a top end and a bottom end, thereby defining a first collecting volume;
an inlet opening disposed through the rear wall proximate the top end;
a cover sheet overlying at least a portion of the top end of the front wall to form a pocket and being secured to the respective wall only along a part of said rim, said pocket positioned to selectively retain said bottom end of the bag or in a folded back position under the cover sheet so as to reduce the size of the bag and to define a second collecting volume, wherein the first collecting volume is at least 25% greater than the second collecting volume.

19. A disposable ostomy receiving bag comprising front and rear walls joined to one another at a rim forming a permanent and continuous seal about an entire perimeter of the bag defined by the rim and having a top end bounded by an uppermost edge of said bag and a bottom end bounded by a lowermost edge of said bag, said top end of the rear wall being provided with an inlet opening, said receiving bag including a cover of a sheet material covering at least part of one of said walls, said cover sheet being secured along a part of said rim so as to selectively receive and retain the bottom end of the bag when folded back, the cover sheet having an unattached or cut edge positioned approximately midway along a longitudinal length of said bag and extending generally perpendicularly to said length, said longitudinal length being that distance between said uppermost edge and said lowermost edge.

20. The receiving bag as claimed in claim 1 wherein the longest dimension of the front wall is reduced by about 50% to about 25% when the bottom end of the bag is folded and extended under said unattached or cut edge.

21. The receiving bag as claimed in claim 18, wherein said cover sheet is provided with an unattached or cut edge extending generally perpendicularly to said longitudinal length of said bag and being placed at a length of from about 50% to about 75% of said longitudinal length.

22. The receiving bag as claimed in claim 21, wherein said unattached or cut edge is positioned approximately midway along said longitudinal length of said bag.

23. The receiving bag as claimed in claim 18, wherein the first collecting volume is at least 50% greater than the second collecting volume.

\* \* \* \* \*